United States Patent
Beaty et al.

(10) Patent No.: US 11,493,473 B2
(45) Date of Patent: Nov. 8, 2022

(54) ELECTRODE BREAK DETECTION

(71) Applicant: Roche Diabetes Care, Inc., Indianapolis, IN (US)

(72) Inventors: Terry A. Beaty, Indianapolis, IN (US); Michael Harrison Wheeler, Zionsville, IN (US)

(73) Assignee: ROCHE DIABETES CARE, INC., Indianapolis, IN (US)

(*) Notice: Subject to any disclaimer, the term of this patent is extended or adjusted under 35 U.S.C. 154(b) by 354 days.

(21) Appl. No.: 16/619,636

(22) PCT Filed: Jun. 6, 2018

(86) PCT No.: PCT/US2018/036183
§ 371 (c)(1),
(2) Date: Dec. 5, 2019

(87) PCT Pub. No.: WO2018/226775
PCT Pub. Date: Dec. 13, 2018

(65) Prior Publication Data
US 2020/0096471 A1  Mar. 26, 2020

Related U.S. Application Data

(60) Provisional application No. 62/516,700, filed on Jun. 8, 2017.

(51) Int. Cl.
G01N 27/327  (2006.01)
(52) U.S. Cl.
CPC ..... G01N 27/3274 (2013.01); G01N 27/3273 (2013.01)

(58) Field of Classification Search
USPC .......... 324/439, 453, 691–693, 719
See application file for complete search history.

(56) References Cited

U.S. PATENT DOCUMENTS

| 4,853,638 A * | 8/1989 | Endou .............. G01N 33/18 324/439 |
| 6,733,655 B1 | 5/2004 | Davies et al. |

(Continued)

FOREIGN PATENT DOCUMENTS

| CN | 105209894 | 12/2015 |
| CN | 105308438 | 2/2016 |

(Continued)

Primary Examiner — Vincent Q Nguyen
(74) Attorney, Agent, or Firm — Woodard, Emhardt, Henry Reeves & Wagner, LLP

(57) ABSTRACT

A method and system for determining a failsafe value for a biosensor having two perimeter electrodes, a distal electrode, and a proximal electrode are disclosed. A liquid measuring medium is applied to a capillary channel of the biosensor. The method includes applying an alternating voltage to the perimeter electrode and the proximal electrode, measuring conductivity to determine a first impedance between the perimeter electrode and the proximal electrode, applying the alternating voltage to the perimeter electrode and the distal electrode, measuring conductivity to determine a second impedance between the perimeter electrode and the distal electrode, determining a value using the first impedance and the second impedance, and providing an error message to the user if the value is out of tolerance. If the value is out of tolerance, then defects or breaks in the electrodes and/or reagent in a reaction area are present and the method disallows the test result.

22 Claims, 14 Drawing Sheets

(56) References Cited

U.S. PATENT DOCUMENTS

| | | |
|---|---|---|
| 7,407,811 B2 | 8/2008 | Burke et al. |
| 7,429,865 B2 | 9/2008 | Dreibholz et al. |
| 7,452,457 B2 | 11/2008 | Burke et al. |
| 7,488,601 B2 | 2/2009 | Burke et al. |
| 7,601,299 B2 | 10/2009 | Beaty et al. |
| 9,039,991 B2 | 5/2015 | Teng et al. |
| 9,149,220 B2 | 10/2015 | Bohm et al. |
| 2012/0111739 A1 | 5/2012 | Pasqua et al. |
| 2016/0059023 A1* | 3/2016 | Freeman ............... A61N 1/3904 607/8 |
| 2017/0082828 A1* | 3/2017 | Sumioka ................ G02B 7/04 |
| 2019/0064100 A1* | 2/2019 | Sode ................ G01N 27/3273 |

FOREIGN PATENT DOCUMENTS

| | | |
|---|---|---|
| CN | 106226379 | 12/2016 |
| WO | WO 2015/187580 | 12/2015 |
| WO | WO 2016/073395 | 5/2016 |

\* cited by examiner

ELECTRODE BREAK DETECTION

TECHNICAL FIELD

The patent application relates generally to engineering and medical diagnostics, and more particularly, it relates to electrochemical biosensors having multiple electrodes arranged that compare impedance measurements between these multiple electrodes to detect electrode breaks and/or reagent defects.

BACKGROUND

Inexpensive disposable electrochemical biosensors generally employ one or two thin electrically conductive layers formed on a flexible or semi-rigid substrate. The electrically conductive layers are formed as electrodes, traces and contact pads on the biosensors wherein resistivity of the conductive traces that connect the reaction zone of the biosensor to the electronic circuitry in a test meter can measure several hundred Ohms or more. This resistance causes a potential drop along the length of the traces, such that the potential presented to the measurement electrodes in the reaction zone is less than the potential applied by the test meter to contact pads of the biosensor in a contact zone of the biosensor. These substrates are susceptible to multiple physical stresses that may stress or break the conductive traces. The stresses may occur during manufacture, shipment, user handling or extreme storage conditions. A stress may be a series of fractures or partial disruptions, creating unexpectedly high trace impedances. A severe stress may create an open circuit or break in one or more electrodes. Electrode breaks in connecting traces might be detected by confirming intact loop resistances or measuring open circuits. Electrode breaks in an active reaction area may be difficult to detect and adversely affect a biosensor's normal operation thereby introducing an error in the reported result.

The manufacturing process of electrochemical biosensors can also include continuously applying thin layers of a reagent film which may be prone to cracking after drying. The cracking in the reagent film may occur during the manufacturing process by any one of various circumstances. For example, the cracking can occur when mechanically cutting near or through the reagent. As another example, the cracking can occur due to physical stresses like twisting, bending, stretching or flexing of the base substrate during manufacturing. As yet another example, cracking can occur when compressing or pinching the base substrate over debris or point defects on guide rollers during the manufacturing process of an electrochemical biosensor.

Additionally, reagent film cracks may also form over time, especially following brief repeated or single extended exposures to high relative humidity. A dry reagent film is somewhat hydrophilic by design as it tends to absorb moisture. As either the exposure time or relative humidity increase, the reagent film may partially hydrate, and physically rearrange upon drying. A reorganized reagent film may be less homogeneous than intended and more prone to separation and/or cracking. A cracked reagent film can extend into the underlying conductive traces and non-conductive supporting base material, depending on the relative adhesion, elasticity, and thickness. If severe, reagent cracks can cause electrode breaks in a biosensor's active reactive area. Electrode breaks may cause a loss of functionality including multiple, gross open circuits, or more subtly alter the area of an active electrode or the working electrode to counter electrode impedance, undetectably and undesirably affecting an accurate correction or computation of the desired analyte concentration.

In some manufacturing processes of electrochemical biosensors, the most common problem are breaks in an outer counter electrode, that may be attributable to exacerbated reagent cracks created near the capillary entrance when cutting through the reagent and flexible base. For example, with two counter electrode segments in the reaction area, a counter electrode area is at least 1.5 times a working electrode area. A defect or break in only the outer counter electrode would have minimal impact on the biosensor's DC response, which should be proportional to the working electrode area. Any defect in the working electrode integrity that affects its functional area would have a linearly negative impact on the DC response, and may unintentionally increase the working electrode to counter electrode impedance. A defective counter electrode segment may not adversely affect the DC response, but can cause the working electrode to counter electrode impedance to appear significantly higher than anticipated, resulting in an over-corrected analyte concentration.

Thus, there is a need for improvement in this field.

SUMMARY

Disclosed is a method of identifying deviations in the surface of a detection or reaction zone in a biosensor to reduce or eliminate the generation of erroneous values. The biosensor includes a reagent positioned in or near a capillary channel, along with any suitable arrangement of electrode structures in the detection and reaction zones. These can include, but are not limited to, a working electrode, one or more counter electrodes, and one or more corresponding sample sufficiency electrodes.

In operation, a low amplitude, high frequency AC signal is imposed between a perimeter electrode and the most proximal electrode, and a first impedance is measured. A similar AC signal is applied between the same perimeter electrode and a more distal electrode, and a corresponding second impedance is measured. Due to their spatial relationship, the impedance between the perimeter electrode and the proximal electrode should be less than the impedance between the perimeter electrode and the distal electrode. Comparing the real portions of these two impedances provides effective proximal or distal electrode break defect detection, over a wide range of test and material conditions. Electrode break detection is enhanced by replicating the sequence using a second perimeter electrode.

A failsafe provides a method or means to identify biosensors with one or more damaged electrodes in the reaction area. By comparing the impedances between one electrode and its two nearest neighbors, a reasonable assessment of the nearer electrode's integrity can be assessed. If the impedance between the base (perimeter) electrode and the most proximal electrode is higher than the impedance between the same base electrode and a more distant electrode, the proximal electrode is most likely defective. The ratio of these resistances should be near unity and is essentially insensitive to normal variations in materials, manufacturing, environmental conditions or test solution. Utilizing low amplitude, high frequency AC signals minimizes the potential for polarizing or disturbing the electrochemical cell used for assessing analyte concentration.

The methods also include providing a biosensor having an electrode support substrate upon which a first electrode is disposed. The first electrode includes a first body portion and a connective neck extending from the first body portion. The electrode support substrate also has a second electrode disposed thereupon, where the second electrode includes a second body portion and an opposite pair of connective necks. Each one of the opposite pair of connective necks extends from a respective end of the second body portion. In addition, at least two sample sufficiency electrodes are provided on the electrode support substrate, each of the sample sufficiency electrodes being positioned along a respective side edge of the electrode support substrate, the sample sufficiency electrodes defining a gap there between. A spacer is also disposed on the electrode support substrate, where the spacer includes at least one edge defining a boundary of a capillary channel formed between a cover and the electrode support substrate. Moreover, the at least two sample sufficiency electrodes surround the first electrode in the capillary channel forming a loop circuit around the first electrode. The second body portion of the second electrode and the opposite pair of connective necks surround the first electrode in the capillary channel forming a loop circuit around the first electrode. Alternative biosensors include other electrode patterns, including biosensors having three or four electrodes, in which the failsafe can be determined.

Aspect 1 concerns a method for error checking a biosensor, comprising applying a liquid measuring medium to a perimeter electrode, a proximal electrode, and a distal electrode on the biosensor, applying an alternating voltage to the perimeter electrode and the proximal electrode, measuring conductivity which is used to determine a first impedance between the perimeter electrode and the proximal electrode, applying said alternating voltage to the perimeter electrode and the distal electrode, measuring conductivity which is used to determine a second impedance between the perimeter electrode and the distal electrode, determining a value using the first impedance and the second impedance, and providing an error message if the value is out of tolerance.

Aspect 2 concerns the method of aspect 1 wherein the perimeter electrode is a sample sufficiency counter electrode.

Aspect 3 concerns the method according to aspect 1 wherein the perimeter electrode is a sample sufficiency working electrode.

Aspect 4 concerns the method according to any one of aspects 1-3 wherein the proximal electrode is one of a working electrode or a counter electrode, and the distal electrode is the other of the working electrode or the counter electrode.

Aspect 5 concerns the method according to any one of aspects 1-4, further comprising detecting a defect in the proximal electrode.

Aspect 6 concerns the method according to any one of aspects 1-5, further comprising detecting a defect in the distal electrode.

Aspect 7 concerns the method according to any one of aspects 1-6, wherein the value is a ratio formed between the first impedance and the second impedance.

Aspect 8 concerns the method according to aspect 7, wherein the providing the error message occurs if the value is less than 1.0, the perimeter electrode is a sample sufficiency working electrode, the proximal electrode is a working electrode, and the distal electrode is a counter electrode.

Aspect 9 concerns the method according to aspect 7, wherein the providing the error message occurs if the value is greater than 1.0, the perimeter electrode is a sample sufficiency counter electrode, the proximal electrode is a working electrode, and the distal electrode is a counter electrode.

Aspect 10 concerns the method of any one of aspects 1-9, wherein the value is a ratio $Z_{REAL}$ (perimeter electrode-proximal electrode)/$Z_{REAL}$ (perimeter electrode-distal electrode) wherein the value being less than 1.0 indicates the distal electrode is defective.

Aspect 11 concerns the method of any one of aspects 1-10, wherein the value is a ratio $Z_{REAL}$ (perimeter electrode-proximal electrode)/$Z_{REAL}$ (perimeter electrode-distal electrode) wherein the value being greater than 1.0 indicates the proximal electrode is defective.

Aspect 12 concerns the method of any one of aspects 1-9, further comprising applying the alternating voltage to a second perimeter electrode and the proximal electrode, measuring conductivity which is used to determine a third impedance between the second perimeter electrode and the proximal electrode, applying the alternating voltage to the second perimeter electrode and the distal electrode, measuring conductivity which is used to determine a fourth impedance between the second perimeter electrode and the distal electrode, determining a second value using the third impedance and the fourth impedance, and providing a second error message if the second value is out of tolerance.

Aspect 13 concerns a measuring instrument for error checking a biosensor, the instrument comprising contacts which electrically connect to a first perimeter electrode, a second perimeter electrode, a proximal electrode, and a distal electrode on the biosensor, electronics which generate a test voltage and detect sensor signals from the first perimeter electrode, the second perimeter electrode, the proximal electrode, and the distal electrode, a processor programmed to apply an alternating voltage to two of the electrodes of the biosensor wherein one of the electrodes is either the first perimeter electrode or the second perimeter electrode, and the second of the electrodes is either the proximal electrode or the distal electrode and measure conductivity which is used to determine a first impedance between the two electrodes, apply the alternating voltage to the remaining two electrodes of the biosensor and measure conductivity which is used to determine a second impedance between the remaining two electrodes, determining a value using the first impedance and the second impedance, and providing an error message if the value is out of tolerance, and an output unit which provides the error message.

Aspect 14 concerns the instrument of aspect 13, wherein the value is a ratio formed between the first impedance and the second impedance.

Aspect 15 concerns the instrument according to any one of aspects 13-14, wherein the providing the error message occurs if the value is less than 1.0, the first perimeter electrode is a sample sufficiency working electrode, the proximal electrode is a working electrode, and the distal electrode is a counter electrode.

Aspect 16 concerns the instrument according to any one of aspects 13-14, wherein the providing the error message occurs if the value is greater than 1.0, the second perimeter electrode is a sample sufficiency counter electrode, the proximal electrode is a working electrode, and the distal electrode is a counter electrode.

Further forms, objects, features, aspects, benefits, advantages, and embodiments of the present invention will become apparent from a detailed description and drawings provided herewith.

DESCRIPTION OF THE SELECTED EMBODIMENTS

Figure 1:
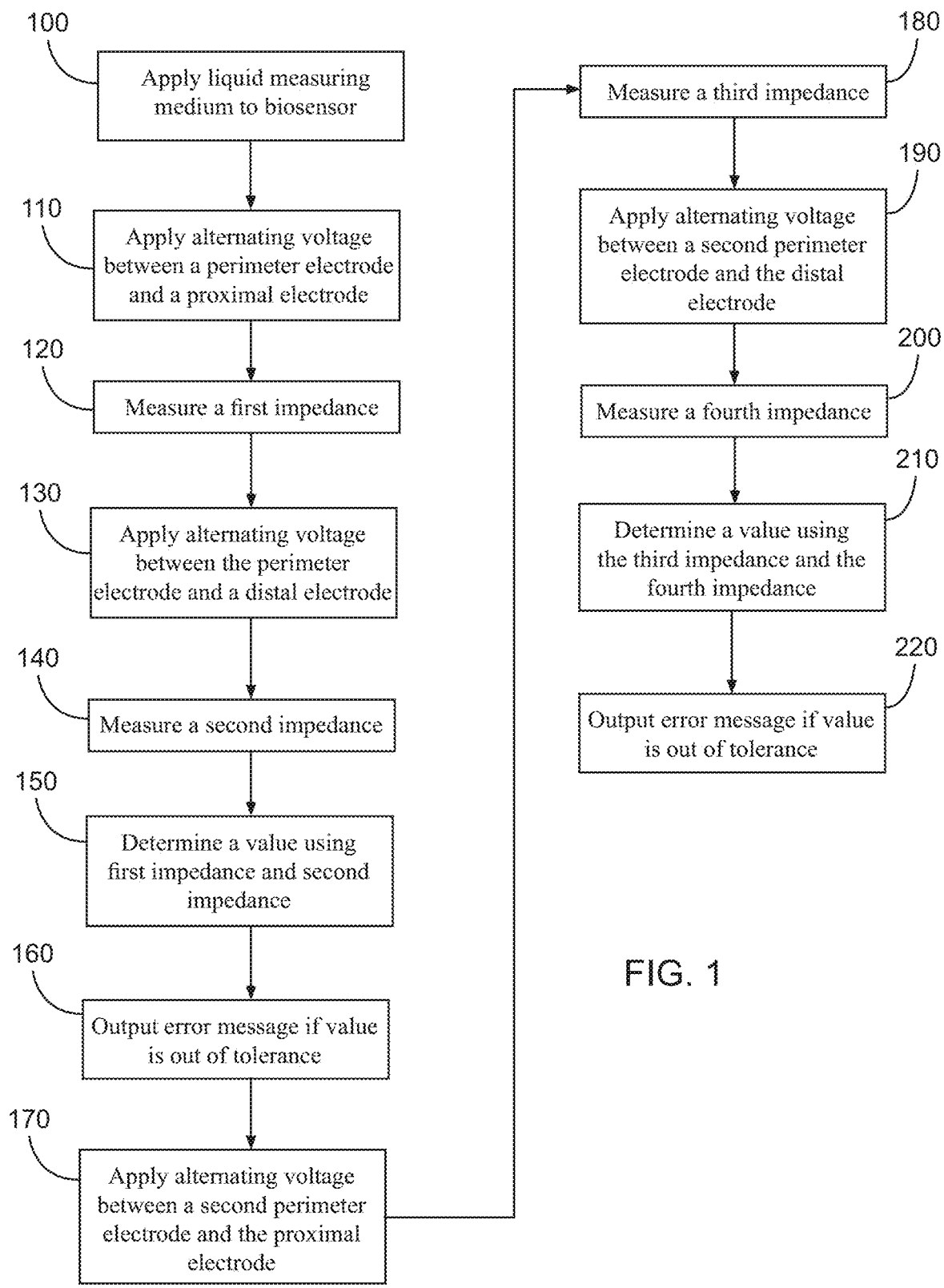
FIG. 1 is a flow chart illustrating one example of a method of identifying deviations in the surface of a detection or reaction zone in a biosensor.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

The present application describes a method which enables the identification of damaged electrodes in the reaction area of a biosensor and thus prevents the generation of erroneous measured values. The actions taken to achieve this result are illustrated in FIG. 1. A capillary channel of the biosensor is filled with a liquid measuring medium at 100. Some examples of a liquid measuring medium include a body fluid such as blood, serum, plasma, saliva, an aqueous environmental sample, a process liquid, an aqueous control, or a calibration liquid.

At 110, an alternating voltage is applied between a perimeter electrode and a proximal electrode at and the alternating voltage (impedance) across the sample is measured at 120 giving a first impedance measurement. An alternating voltage is also applied between the perimeter electrode and a distal electrode at 130 and a second impedance measurement across the sample is measured in step 140. The real portions of these first and second impedances are determined and compared at 150. An output error or failsafe error is provided to the user at 160 if the values from step 150 are out of tolerance. As discussed below, this tolerance can be any suitable value such as a value greater than about 1.0, greater than about 1.043, greater than about 1.100, or more. Values between 1.0 and about 1.1 may be considered nominal, while values less than about 1.0, or less than about 0.097 may indicate failures as well.

Electrode break detection is enhanced by replicating this general sequence for any of multiple different electrodes in a biosensor. At 170 the alternating voltage is applied between a second perimeter electrode and the proximal electrode and the alternating voltage (impedance) across the sample is measured at 180 giving a third impedance measurement. At 190, the alternating voltage is applied between the second perimeter electrode and the distal electrode and the impedance across the sample is measured at 200 yielding a fourth impedance measurement. The real portions of these two impedances are determined and compared at 210. An output error or failsafe error is provided to the user at 220 if the values from 210 are out of tolerance. As discussed herein, this tolerance can be any suitable value such as a value greater than 1.0 or lesser than 1.0 depending upon which electrode is being tested for a defect.

FIG. 1 illustrates one example of actions that may be taken to irregularities in biosensor electrodes. The disclosed impedance measurements and comparisons may be performed as shown in FIG. 1, or in any other suitable order. For example, the impedance between the perimeter electrode and distal electrode may be measured before the impedance between the perimeter electrode and proximal electrode. Similarly, the impedance between the second perimeter electrode and the distal electrode may be measured before the impedance between the second perimeter electrode and the proximal electrode. Also, additional impedances may be measured between electrodes which may be present in a biosensor that has additional electrodes.

In other cases, a biosensor may have fewer electrodes and thus some actions shown in FIG. 1 may be omitted accordingly.

A system for carrying out the method according to the application FIG. 1 includes a biosensor and a measuring instrument. The measuring instrument contains at least one source of alternating voltage and contacts for connecting to the electrodes in the biosensor. The measuring instrument also includes control and measuring electronics to generate voltages on the contacts and to detect the sensor signals, and at least one processor to compare and correlate the sensor signals on the basis of a program for carrying out the method according to the application. The measuring instrument further includes an output unit, e.g., lamp, light-emitting diode, display, data interface, printer, printer connection, etc., for providing an error message when the value is out of tolerance. Software updates can be provided to the measuring instrument to fine tune the tolerances and other aspects of the measuring process.

Figure 2:
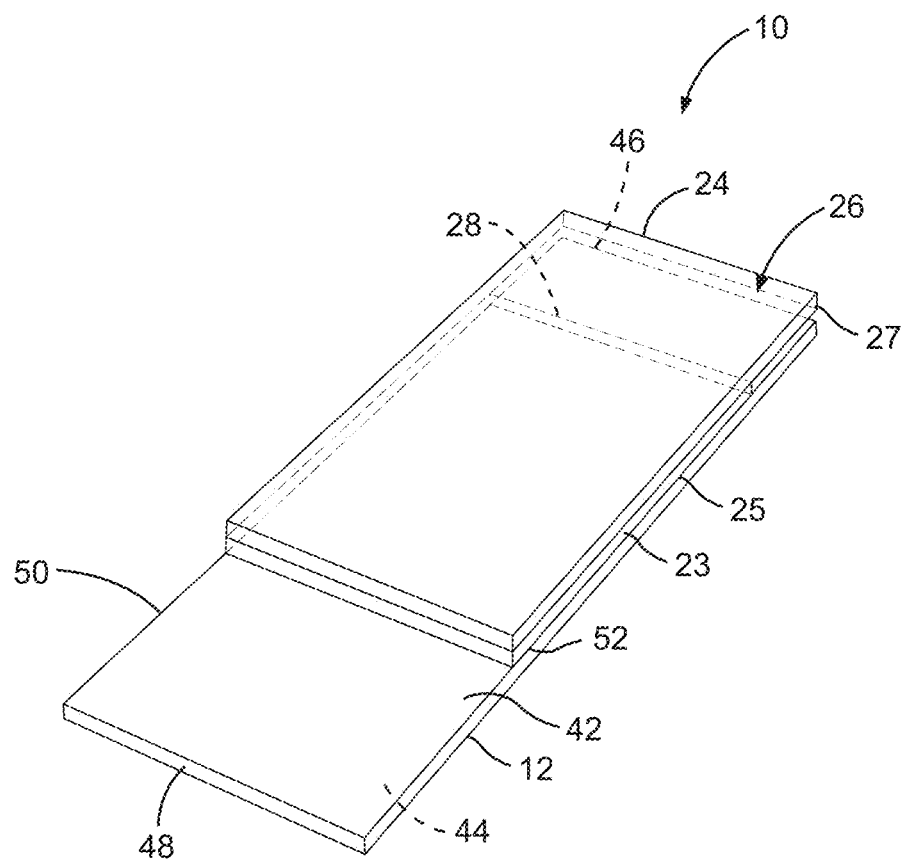
FIG. 2 is a perspective view of an exemplary biosensor.
Figure 3:
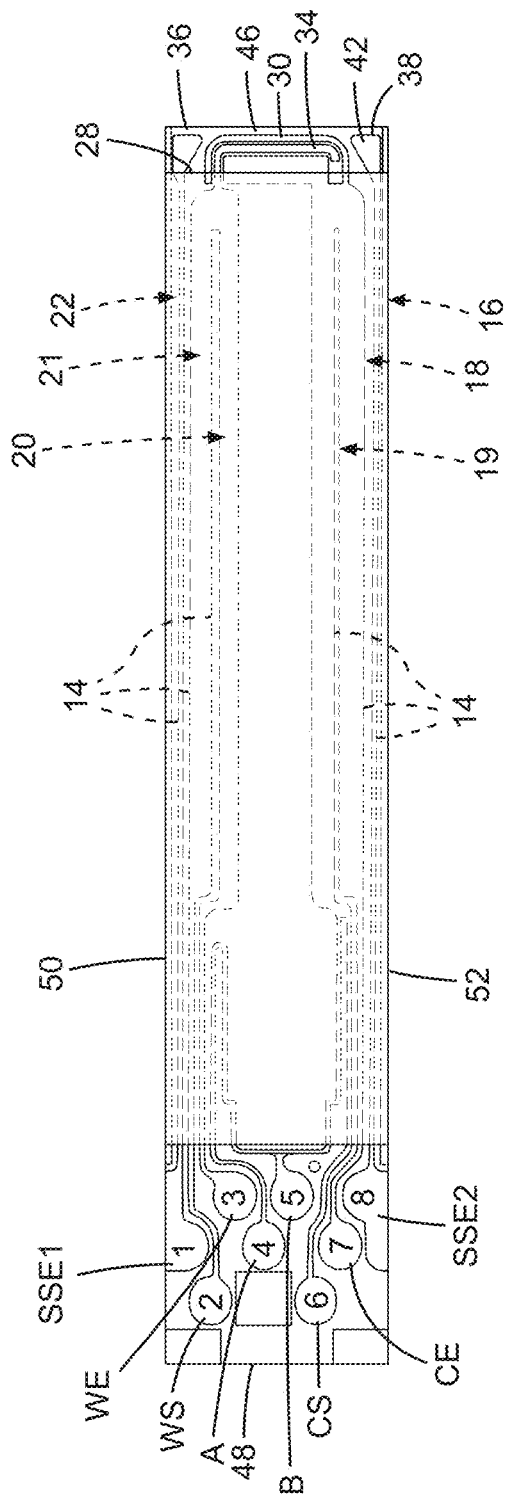
FIG. 3 is a plan view of the biosensor shown in FIG. 2.

FIG. 2 shows a perspective view of an exemplary biosensor at 10. FIG. 2 is a plan view of the biosensor 10 shown in FIG. 2. FIG. 3 is a plan view of a portion of the biosensor 10 shown in FIG. 2 showing an exemplary electrode arrangement. In the exemplary embodiment, the biosensor 10 includes an electrode-support substrate 12, an electrical conductor 14 formed on the electrode-support substrate 12 that defines a plurality of electrode traces 16, 18, 19, 20, 21 and 22, a spacer 23 positioned on the electrode-support substrate 12, and a cover 24 positioned on the spacer 23. In some instances, the electrical conductor 14 may form any number of electrode traces that enable the biosensor 10 to function as described herein. In FIGS. 2 and 3, however, the spacer 23 is not shown for clarity.

As shown in FIGS. 1 and 2, the biosensor 10 can have a substantially rectangular shape; however, any one of a number of forms that enable the biosensor 10 to function as described herein also are contemplated. In addition, the biosensor 10 can be any one of a plurality produced from rolls of material, sheets of material or any other material stock in accordance with the principles of this disclosure. In general, the material selection for fabricating the biosensor 10 includes any material that is sufficiently flexible for roll processing, but is rigid enough to give a useful stiffness to the finished biosensor 10.

In the exemplary embodiment, the electrode-support substrate 12 of the biosensor 10 includes a first surface 42 facing the spacer 23 and a second surface 44 opposite the first surface 42. Moreover, the electrode-support substrate 12 has opposite first and second ends 46, 48 and opposite side edges 50, 52 that extend between the first and second ends 46, 48. In some instances, the first and second ends 46, 48 and the opposite side edges 50, 52 of the electrode-support substrate 12 form a generally rectangular shape. Alternatively, the first and second ends 46, 48 and the opposite side edges 50, 52 may be arranged to form any one of a variety of shapes and sizes that enable the biosensor 10 to function as described herein. In some instances, the electrode-support substrate 12 can be fabricated of a flexible polymer including, but not limited to, a polyester or polyimide, such as polyethylene naphthalate (PEN). Alternatively, the electrode-support substrate 12 can be fabricated from any other suitable materials that enable the electrode-support substrate 12 to function as described herein.

In the exemplary embodiment, the electrical conductor 14 forming the electrode traces 16, 18, 19, 20, 21 and 22 is provided on the first surface 42 of the electrode-support substrate 12. The electrical conductor 14 may be fabricated from materials including, but not limited to, aluminum, carbon (e.g., graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., highly doped polycrystalline silicon), silver, tantalum, tin, titanium, tungsten, uranium, vanadium, zinc, zirconium, and combinations thereof. In some instances, the electrode traces 16, 18, 19, 20, 21 and 22 are isolated from the rest of the electrical conductor 14 by laser ablation or laser scribing, both of which are well known in the art. In this manner, the electrode traces 16, 18, 19, 20, 21 and 22 can be fabricated by removing the electrical conductor 14 from an area extending around the electrodes either broadly, such as by broad field ablation, or minimally, such as by line scribing. Alternatively, the electrode traces 16, 18, 19, 20, 21 and 22 may be fabricated by other techniques such as, for example, lamination, screen-printing, photolithography, etc.

In the exemplary embodiment, biosensor 10 is a full width end dose ("FWED"; having a capillary channel bounded on one side) biosensor, which has a capillary channel 26 or an inlet at the first end 46 of the electrode-support substrate. It is contemplated, however, that the capillary channel 26 also can be a conventional capillary channel (i.e., bounded on more than one side). In a FWED biosensor, the spacer 23 extends between the opposite side edges 50, 52 of the electrode-support substrate 12 to form the capillary channel in part with a cover. It is contemplated that the spacer 23 may be fabricated of a single component or even a plurality of components. Regardless, the spacer 23 should include an end edge 28 substantially parallel to and facing the first end 46 of the electrode-support substrate 12, thereby defining a boundary of a capillary channel 26 by extending across the entire width of the electrode-support substrate 12. Alternatively, and as noted above, the end edge 28 may include multiple portions located between the first and second ends 46, 48 and the opposite side edges 50, 52 of the electrode-support substrate 12 to form a generally U-shaped pattern to define the boundary of the capillary channel 26 having a sample inlet at the first end 46 of the biosensor 10 (not shown). Other suitable embodiments contemplate an end edge 28 that forms hemi-ovular, semi-circular, or other shaped capillary channels, and the one or more of the portions of end edge 28 may include linear or non-linear edges along all or part of its length (not shown).

The spacer 23 is fabricated from an insulative material such as, for example, a flexible polymer including an adhesive-coated polyethylene terephthalate (PET)-polyester. One particular non-limiting example of a suitable material includes a white PET film, both sides of which are coated with a pressure-sensitive adhesive. The spacer 23 may be constructed of a variety of materials and includes an inner surface 25 that may be coupled to the first surface 42 of the electrode-support substrate 12 using any one or a combination of a wide variety of commercially available adhesives. Additionally, when first surface 42 of the support substrate 12 is exposed and not covered by the electrical conductor 14, the cover 24 may be coupled to support the electrode-substrate 12 by welding, such as heat or ultrasonic welding. It also is contemplated that first surface 42 of the electrode-support substrate 12 may be printed with, for example, product labeling or instructions (not shown) for use of the biosensors 10.

Further, in the exemplary embodiment, the cover 24 extends between the opposite side edges 50, 52 of the electrode-support substrate 12 and extends to the first end 46 of the electrode-support substrate 12. Alternatively, the cover 24 may extend beyond the first end 46 a predefined distance that enables the biosensor 10 to function as described herein. In the exemplary embodiment, the capillary channel 26 is therefore defined as the space between the cover 24 and the electrode-support substrate 12, bounded by the first end 46 and the opposite side edges 50, 52 of the electrode-support substrate 12 and the end edge 28 of the spacer 23.

The cover 24 can be fabricated from an insulative material such as, for example, a flexible polymer including a PET-polyester. One particular non-limiting example of a suitable material includes a transparent or translucent PET film. The cover 24 may be constructed of a variety of materials and includes a lower surface 27 that may be coupled to the spacer 23 using any one or a combination of a wide variety of commercially available adhesives. Additionally, the cover 24 may be coupled to the spacer 23 by welding, such as heat or ultrasonic welding.

In the exemplary embodiment, the biosensor 10 includes an outer counter electrode 30 and an inner counter electrode 32 extending across the capillary channel 26 and coupled to electrode traces 18 and 19. In addition, the biosensor 10 includes a working electrode 34 that is positioned in capillary channel 26 between the counter electrodes 30, 32. The working electrode 34 is coupled to traces 20 and 21. Moreover, the biosensor 10 also includes a sample sufficiency working electrode (SSWE) 36 coupled to electrode trace 22 and a sample sufficiency counter electrode (SSCE) 38 coupled to electrode trace 16 positioned in the capillary channel 26. The SSWE 36 and the SSCE 38 are positioned adjacent the edges of the electrode-support substrate 12.

In the exemplary embodiment, the SSCE 36 is coupled to contact pad SSE1 by electrode trace 22, and the SSCE 38 is coupled to contact pad SSE2 by electrode trace 16. Likewise, the outer counter electrode 30 and the inner counter electrode 32 are coupled to electrode traces 18, 19. As shown in FIG. 3, the electrode trace 18 is coupled to contact pad CE, and the electrode trace 19 is coupled to contact pads CS, B and A. Moreover, the working electrode 34 is coupled to electrode traces 20 and 21, where electrode trace 20 is coupled to the contact pad WE, and the electrode trace 21 is coupled to the contact pad WS. These contact pads provide a conductive area upon the biosensor 10 to be contacted by a connector contact of a test meter (not shown) once the biosensor 10 is inserted into the test meter. It is further contemplated that the configuration of the electrodes, the number of electrodes, as well as the spacing between the electrodes may vary in accordance with the disclosure. Consequently, biosensor 10 may include more or fewer than the number of electrodes illustrated herein.

Figure 4:
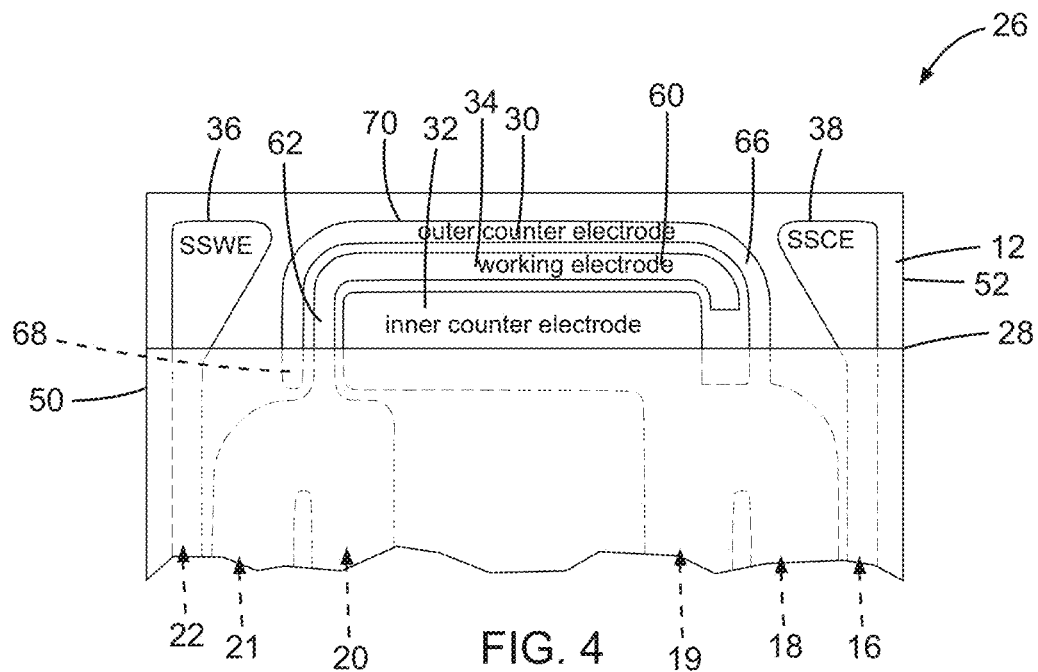
FIG. 4 is a plan view of a portion of the biosensor shown in FIG. 2 showing an exemplary electrode arrangement.

In the exemplary embodiment, the working electrode 34 defines an effective working electrode area in the capillary channel 26. The effective working electrode area is the area of the working electrode that contacts a fluid sample in the capillary channel 26 when the capillary channel 26 includes sufficient volume of the fluid sample to initiate a measurement sequence. As seen in FIG. 4, the working electrode 34 includes a main body portion 60 extending laterally between the opposite side edges 50, 52 of the electrode-support substrate 12, and a connective neck 62 extending from main body portion 60 across the edge 28 of capillary channel 26 (i.e., transversely from the main body portion 60 toward the end 48 of biosensor 10 opposite capillary channel 26). The connective neck 62 is coupled to the electrode traces 20, 21 that extend along one side of the electrode-support substrate 12. The spacer 23 is positioned such that the edge 28 extends across the connective neck 62 and so that the main body portion 60 is located entirely within the capillary channel 26. Electrochemical detection reagents can be positioned on the working electrode 34, which provide electrochemical probes for specific analytes. The choice of specific reagents depends on the analyte(s) to be measured, which are well known in the art. An example of a detection reagent that may be used in the biosensor 10 is a reagent for measuring glucose from a body fluid sample such as a whole blood sample.

In the exemplary embodiment, the inner counter electrode 32 and the outer counter electrode 30 are connected to electrode traces 18, 19 that extend along one side of the electrode-support substrate 12. The outer counter electrode 30 extends laterally between the opposite side edges 50, 52 of the electrode-support substrate 12, and includes an extension trace 68 and a connective neck 62 that each extend from a main body portion 70 across the edge 28 of capillary channel 26 (i.e., transversely from the main body portion 70 toward the end 48 of biosensor 10 opposite capillary channel 26). Moreover, the edge 28 of the capillary channel 26 extends along and partially overlaps the inner counter electrode 32. In some instances, electrochemical detection reagents can be positioned on the inner counter electrode 32 and the outer counter electrode 30. As noted above, the detection reagents provide electrochemical probes for specific analytes and are well known in the art, especially for measuring glucose.

Figure 5:
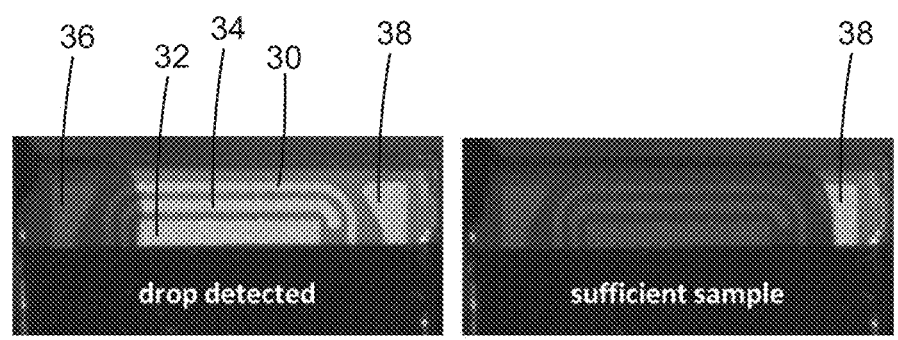
FIG. 5 is a plan view of the portion of the biosensor shown in FIG. 4 showing a sample application.

The biosensor 10 illustrates an active electrode area that utilizes a reasonably symmetric geometry in FIGS. 3 and 4. As illustrated in FIG. 5, a sample application is first detected by rapidly measuring the impedance between the outer counter electrode 30 and working electrode 34. Once a minimum conductivity is exceeded, sample sufficiency is subsequently similarly determined by rapidly measuring the impedance between the SSCE 38 and SSWE 36. If the conductivity between the SSCE 38 and the SSWE 36 exceeds a programmable threshold within a programmable timeout interval, the biosensor 10 is deemed acceptably dosed (FIG. 5), and an analyte concentration measurement sequence may begin. If a minimum sample sufficiency conductivity is not exceeded with an allowed time, an error is indicated and the sequence is aborted. The SSCE 38 and the SSWE 36 are principally intended to ensure the outer counter electrode 30 and working electrode 34 are adequately covered to reliably proceed with an analyte measurement.

The biosensor 10 in FIGS. 2-4 illustrates merely one example of many possible arrangements of electrodes for electrochemical detection of specific analytes. However, the principles discussed are applicable to any suitable geometry of electrodes in a biosensor. For example, the method can be applied to biosensors with multiple working electrodes and a single counter electrode, or for biosensors with any suitable configuration of proximal, distal and perimeter electrodes. Similarly, the disclosed method can be effective for biosensors with one or more counter electrodes, one or more working electrodes, and any suitable arrangement of electrodes performing a function similar to the SSCE and SSWE electrodes disclosed. No limitation should be implied based on specific naming conventions for electrodes used in the disclosed examples. The terms "distal", "proximal", "working", and abbreviations such as "SSWE" and "SSCE" are exemplary as well rather than restrictive. Other biosensors and measuring devices may use different names for the various electrodes, but the principles disclosed herein still apply.

Figure 6:
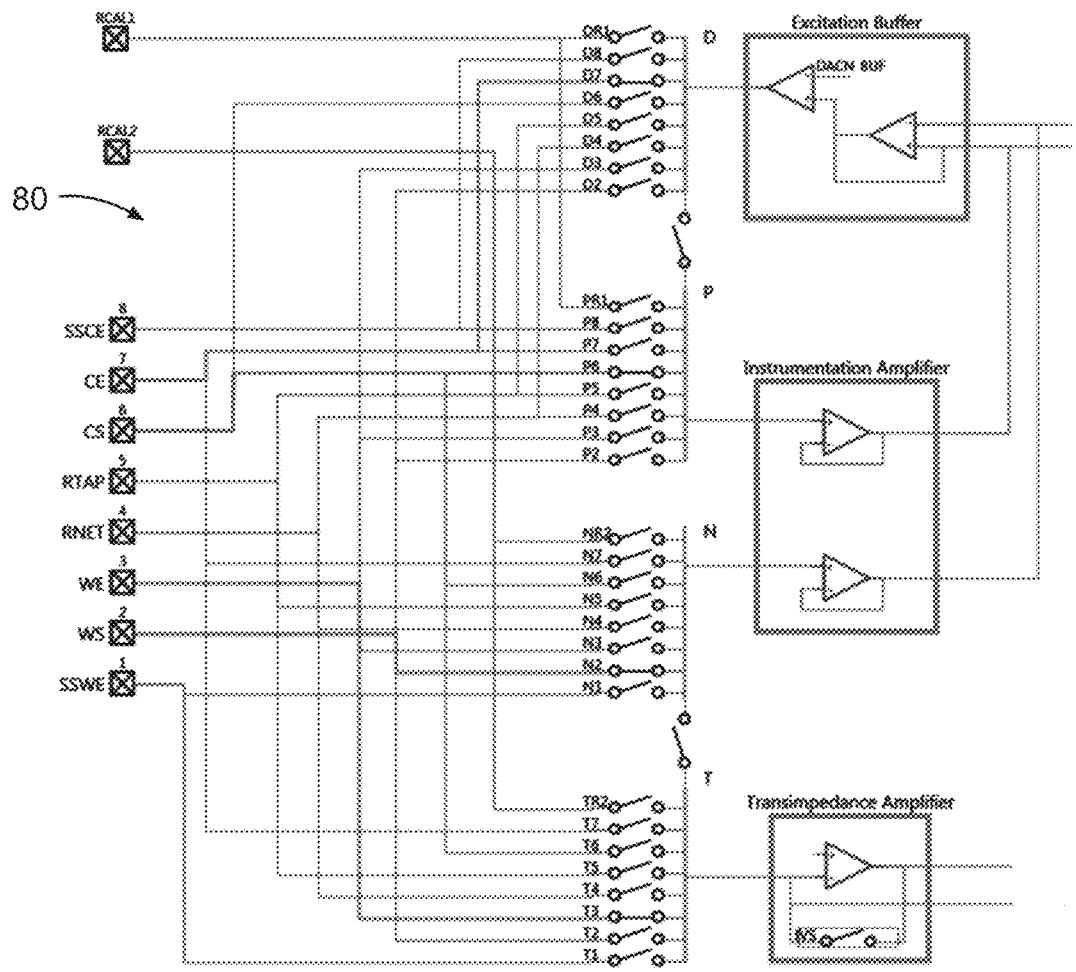
FIG. 6 is a plan view of an analog switch matrix in a test meter or other device configured to use the biosensor shown in FIG. 2.

The test meter or other device configured to use the biosensor 10 includes an analog switch matrix 80 that allows programmable connection of individual or multiple electrode contacts to the desired potentiostat function (FIG. 6). The switch matrix 80 is similar to a crosspoint switch, permitting reconfigurable connection of the potentiostat's excitation and response functions to a calibration load (RCAL) or any combination of up to seven biosensor contacts. One or more sensor contacts may be connected together to join or extend a desired function. The instrumentation amplifier's inputs select the positive and negative excitation feedback (sense) inputs. These inputs may be selected from a biosensor contact by closing the appropriate P and/or N switches, or as local feedback behind the switch array by closing one or both of the vertical switches in FIG. 6. The switch matrix 80 enables the potentiostat to interrogate the outer counter electrode 30 and working electrode 34 with working sense and counter sense connections for remote excitation sense detection, then connect to the SSWE 36 and the SSCE 38. The switch matrix 80 permits programmable selection of multiple alternate electrode connections for detecting unintended biosensor connections (shorts) or measurement of other networks formed on the electrode-support substrate 12. The test meter or other device configured to use the biosensor 10 is configured to apply a signal such as, for example, an AC signal, to the biosensor 10 to check the electrical continuity along the outer counter electrode 30 and/or the working electrode 34 prior to using the biosensor 10 to analyze biological fluids. A discontinuity along the outer counter electrode 30 and/or the working electrode 34 results in an indication that the biosensor 10 has likely sustained physical damage. Thus, the test meter can alert the user that the biosensor 10 has failed the integrity check, and therefore should be discarded (i.e., test result failsafed). If the biosensor 10 passes the integrity check (i.e., the test meter confirms continuity along the outer counter electrode 30 and/or the working electrode 34), then the meter can alert the user that the biosensor 10 is safe to use.

Figure 7:
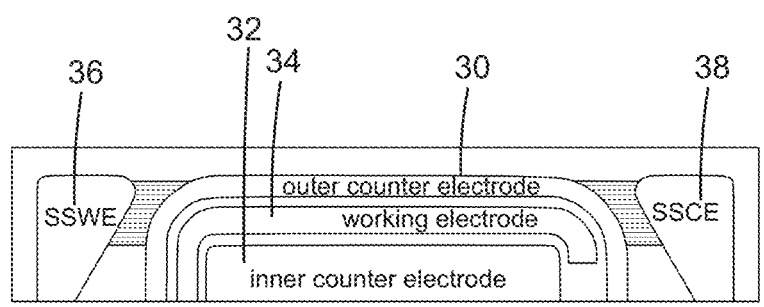
FIG. 7 is a plan view of the portion of the biosensor shown in FIG. 4 showing an impedance measurement from SSCE to the counter electrode and an impedance measurement from SSWE to the counter electrode being measured.

In a first failsafe, a method uses the active electrode's spatial symmetry to detect a break in the outer counter electrode 30. Generally, the impedance between either the SSWE 36 or the SSCE 38 and the outer counter electrode 30 should be more influenced by the outer counter electrode 30 due to the closeness or vicinity of the outer counter electrode 30 to either of the SSWE 36 and the SSCE 38. Since both impedances are comparably influenced by reagent flow rate, solution conductivity, environmental conditions and metal resistivity, the ratio of $|Z|SSWE-CE$ to $|Z|_{SSCE-CE}$ should track over these conditions. In one embodiment, the AC signal of amplitude is significantly less than the DC potential difference which would even partially generate a glucose dependent current is applied as described next. A low amplitude, high frequency AC signal is applied between the outer counter electrode 30 and a perimeter electrode such as SSWE 36 and the impedance is measured as the absolute value of $|Z|_{SSWE-CE}$. Next the low amplitude, high frequency AC signal is applied between the outer counter electrode 30 and a perimeter electrode such as SSCE 38 and the impedance is measured as the absolute value of $|Z|_{SSCE-CE}$. The impedance from the SSCE 38 to outer counter electrode 30 and the impedance from the SSWE 36 to outer counter electrode 30 are compared. If there is not a break or defect in the outer counter electrode 30, then the impedance between the outer counter electrode 30 and the perimeter electrode such as SSWE 36 should be very similar or about equal to another perimeter electrode of equal area and spacing such as SSCE 38 and the outer counter electrode 30 as illustrated in FIG. 7. If the $|Z|_{SSWE-CE}$ and $|Z|_{SSCE-CE}$ are equal or approximately equal, and the outer counter electrode 30, inner counter electrode 32, working electrode 34, reagent and sample collectively appear symmetrical with respect to the SSWE 36 and SSCE 38, then the outer counter electrode 30 may be presumed intact. In other words, the outer counter electrode 30 does not have any breaks or defects and there is no failsafe.

Figure 8:
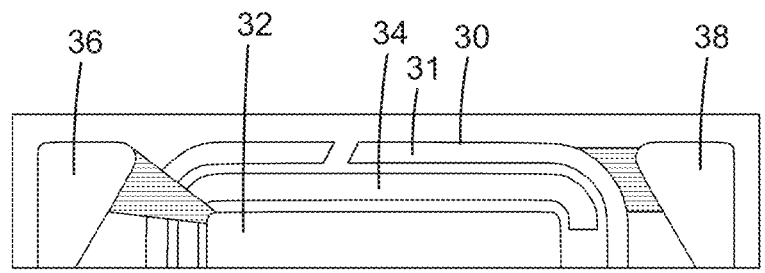
FIG. 8 is a plan view of the portion of the biosensor shown in FIG. 4 with a defect in the counter electrode showing an impedance measurement from SSCE to the counter electrode and an impedance measurement from SSWE to the counter electrode being measured.

FIG. 8 depicts the equivalent coupling as FIG. 7 but illustrates the outer counter electrode 30 is broken somewhere near a middle portion 31 of the outer counter electrode 30. The impedance from SSCE 38 to outer counter electrode 30 in FIG. 8 would be comparable to the similar measurement in FIG. 7, but the impedance from SSWE 36 to outer counter electrode 30 in FIG. 8 would be higher since the SSWE 36 is now located further from (a portion of) the inner counter electrode 32. The effect would be even more pronounced if the counter electrode had only one outer counter electrode 30 and did not include the inner counter electrode 32. If $|Z|_{SSWE-CE}$ is greater than $|Z|_{SSCE-CE}$, then most likely the outer counter electrode 30 is damaged or broken and an open circuit has formed and a failsafe is provided to the user.

In a second failsafe, a method uses the active electrode's spatial symmetry to detect a break in the working electrode 34. In one embodiment, the AC signal of amplitude significantly less than the DC potential difference which would even partially generate a glucose dependent current is applied as described next. A low amplitude, high frequency AC signal is applied between the working electrode 34 and a perimeter electrode such as SSWE 36 and the impedance is measured as $|Z|_{SSWE-WE}$. Next the low amplitude, high frequency AC signal is applied between the working electrode 34 and a perimeter electrode such as SSCE 38 and the impedance is measured as $|Z|_{SSCE-WE}$. The absolute values of the impedance from the SSCE 38 to working electrode 34 and the impedance from the SSWE 36 to working electrode 34 are compared. The side to side impedance between the working electrode 34 and a perimeter electrode such as SSWE 36 should be comparable to the working electrode 34 and another perimeter electrode such as SSCE 38 of similar area and spacing. If $|Z|_{SSWE-WE}$ is equal or approximately equal to $|Z|_{SSCE-WE}$, then the working electrode 34 may be presumed intact. In other words, the working electrode 34 does not have any breaks or defects and there is no failsafe. If $|Z|_{SSCE-WE}$ is greater than $|Z|_{SSWE-WE}$, then most likely the working electrode 34 is damaged or broken and an open circuit has formed and a failsafe is provided to the user.

Figure 9:
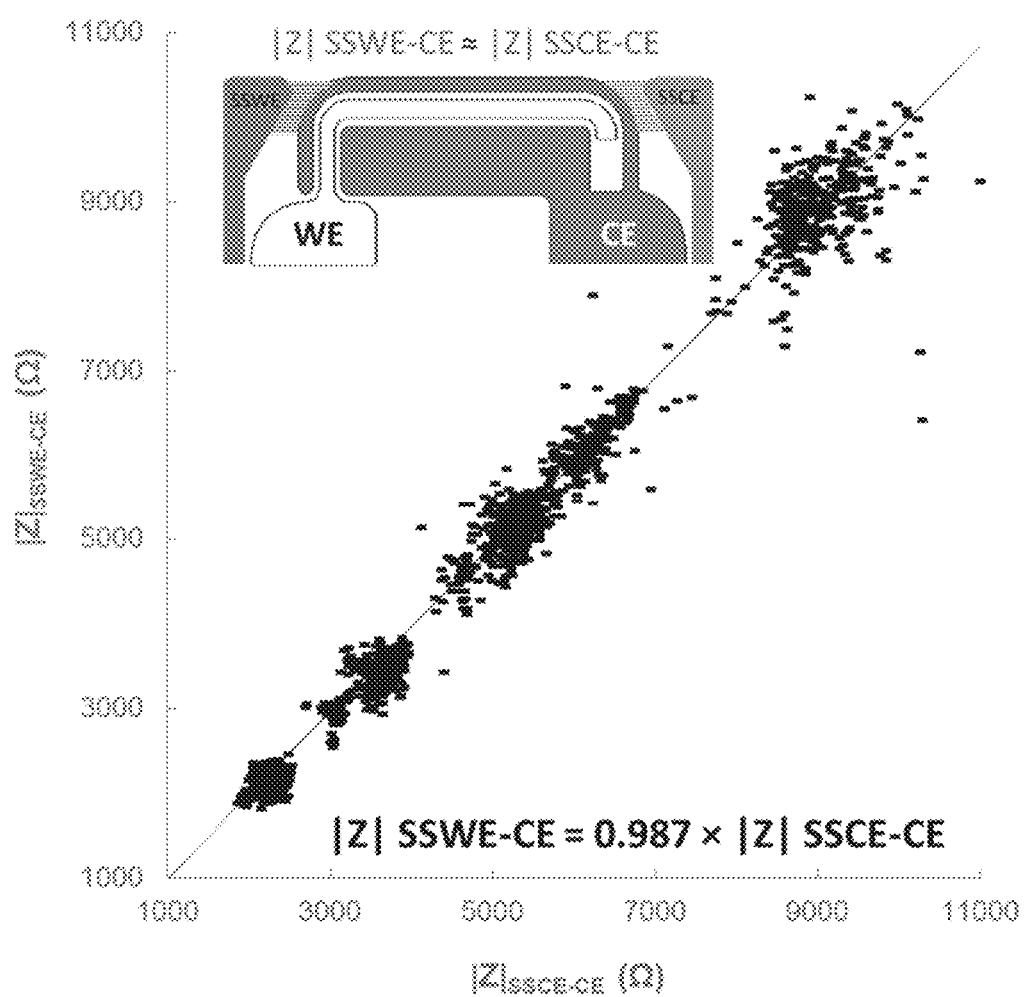
FIG. 9 plots test results of $|Z|_{SSWE-CE}$ plotted along the y-axis measured in Ohms and $|Z|_{SSCE-CE}$ plotted along the x-axis measured in Ohms for the biosensor shown in FIG. 4.

FIG. 9 depicts test results of $|Z|_{SSWE-CE}$ plotted along the y-axis measured in Ohms and $|Z|_{SSCE-CE}$ plotted along the x-axis measured in Ohms for presumably undamaged, normal biosensors 10 over a broad range of sample conductivity, base metal thickness, reagent film thickness, pilot age, storage condition, manufacturing variations and test temperatures. It was discovered that the impedance ratio is approximately equal to 1 and in one form is about 0.987.

Figure 10:
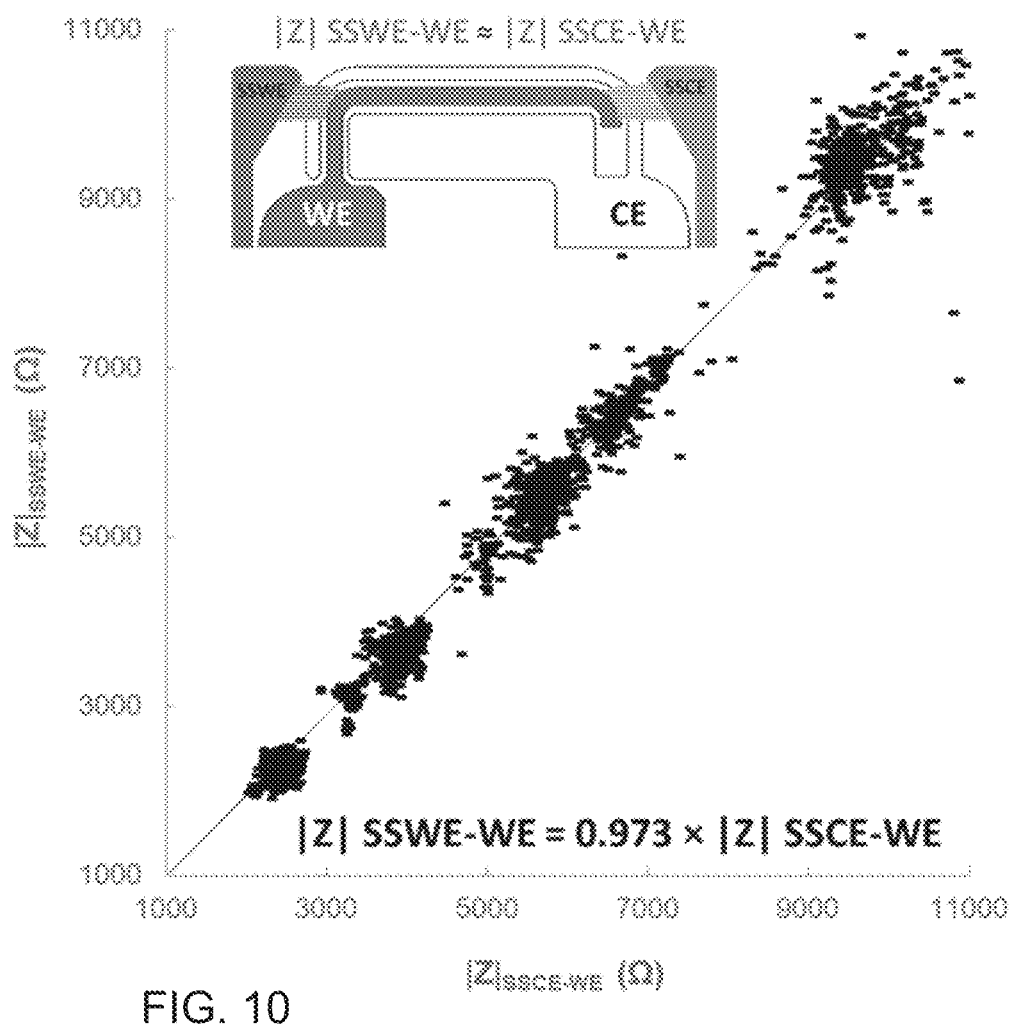
FIG. 10 plots test results of $|Z|_{SSWE-WE}$ plotted along the y-axis measured in Ohms and $|Z|_{SSCE-WE}$ plotted along the x-axis measured in Ohms for the biosensor shown in FIG. 4.
Figure 11:
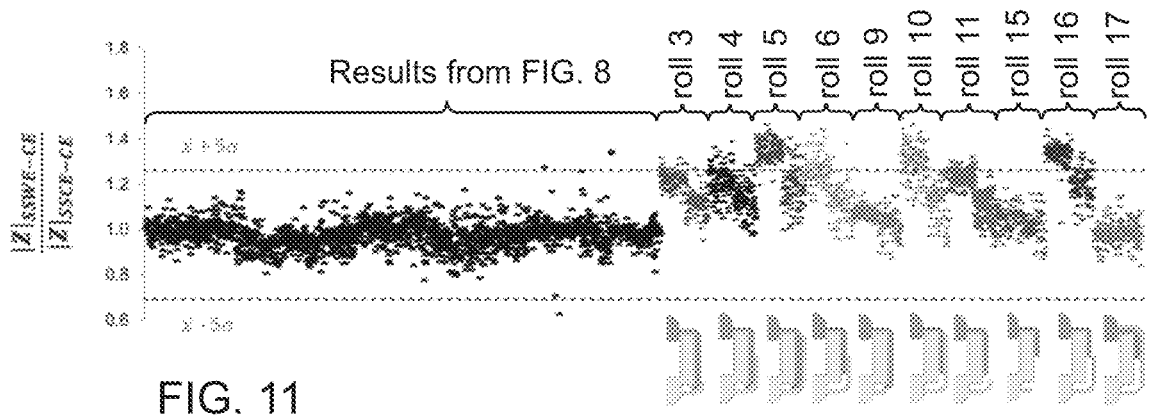
FIG. 11 plots the test results from FIG. 9 with x±5σlimits and the test results from biosensors shown in FIG. 4 constructed with various electrode breaks.

FIG. 10 depicts test results of $|Z|_{SSWE-WE}$ plotted along the y-axis measured in Ohms and $|Z|_{SSCE-WE}$ plotted along the x-axis measured in Ohms for presumably undamaged, normal biosensors 10 over a broad range of sample conductivity, base metal thickness, reagent film thickness, pilot age, storage condition, manufacturing variations and test temperatures. It was discovered that the impedance ratio is approximately equal to 1 and in one form is about 0.973.

Figure 12A:
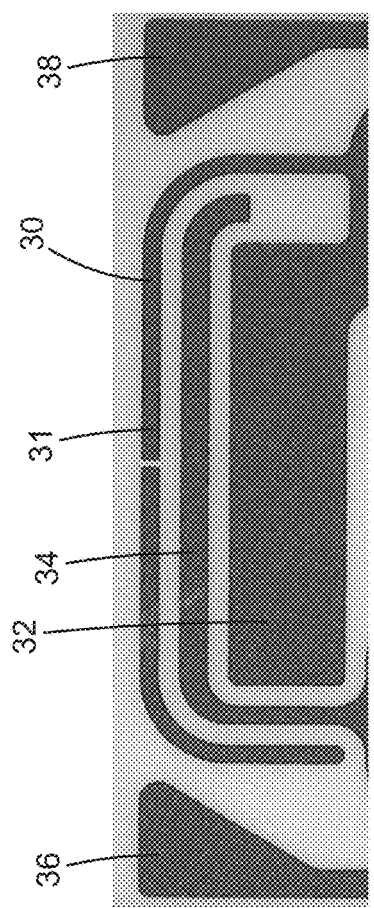
FIG. 12A is a plan view of a portion of the biosensor shown in FIG. 4 with a defect in the counter electrode.
Figure 12B:
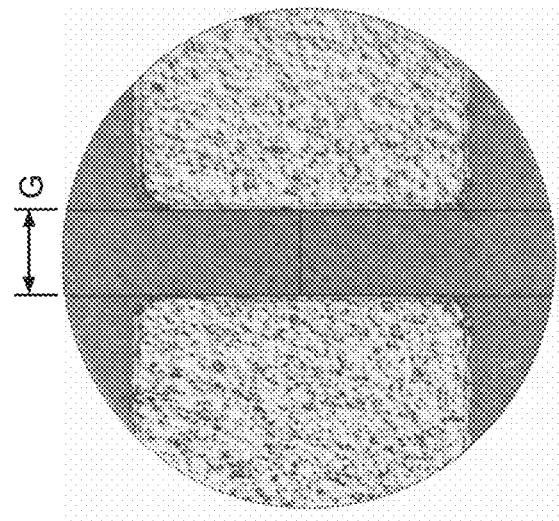
FIG. 12B is a plan view of a measurement of the defect in the counter electrode of FIG. 12A.
Figure 12C:
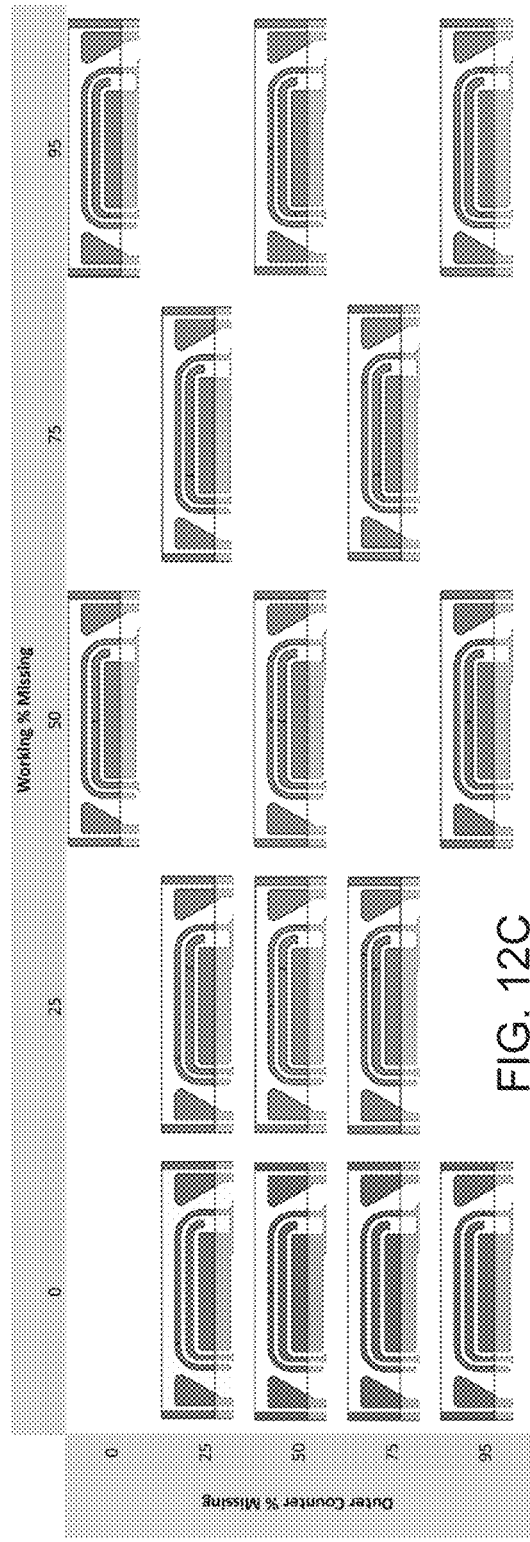
FIG. 12C is a graph representing different locations for defects in the counter electrode and/or the working electrode of the biosensor shown in FIG. 4 to simulate missing 0%, 25%, 50%, 75%, or 95% of any of these electrodes.

Regarding FIG. 9 and FIG. 10, the near 1:1 relationship for both sets of test results is fairly noisy. FIG. 10 plots the $|Z|_{SSWE-CE}$ to $|Z|_{SSCE-CE}$ ratios for the same biosensors 10 that were tested in FIG. 9 with x±5σ limits. FIG. 10 also plots the test results from biosensors 10 constructed with various electrode breaks that are illustrated in FIG. 12C as described next. An effective failsafe's objective would be to reliably identify all or nearly all damaged sensors exceeding these limits.

Testing Results

A first test pilot was conducted with biosensors 10 wherein each of the biosensors included a different location of intentional defects in any of the working electrode 34 and/or the outer counter electrode 30. The intentional defects included an electrode break or gap G in the working electrode 34 and/or the outer counter electrode 30 having a width of about 30 µm. A total of 15 different locations of intentional defects or electrode breaks in the electrode structures are illustrated in FIGS. 12A, 12B, and 12C. The variations or electrode breaks were designed to simulate missing 0%, 25%, 50% 75% and 95% of either the working electrode 34 and/or the outer counter electrode 30 illustrated in FIG. 12C. FIG. 12A also includes one example (designated roll 4) shown in an enlarged view. The $|Z|_{SSWE-CE}$ to $|Z|_{SSCE-CE}$ impedance ratios for ten variations of electrode breaks in the working electrode 34 and/or the outer counter electrode 30 of the biosensors 10 tested from FIG. 12C are plotted in FIG. 10 and labeled roll 3, roll 4, roll 5, roll 6, roll 9, roll 10, roll 11, roll 15, roll 16, and roll 17. The test solutions included multiple glucose concentrations of aqueous linearity solution and nominal blood at room temperature that were used and applied to the biosensors 10 labeled roll 3, roll 4, roll 5, roll 6, roll 9, roll 10, roll 11, roll 15, roll 16, and roll 17. Summarizing from FIG. 10, 82.3% of the test pilot $|Z|_{SSWE-CE}$ to $|Z|_{SSCE-CE}$ ratios are within the x±5σlimits, or no better than a 17.7% effective failsafe.

Figure 13:
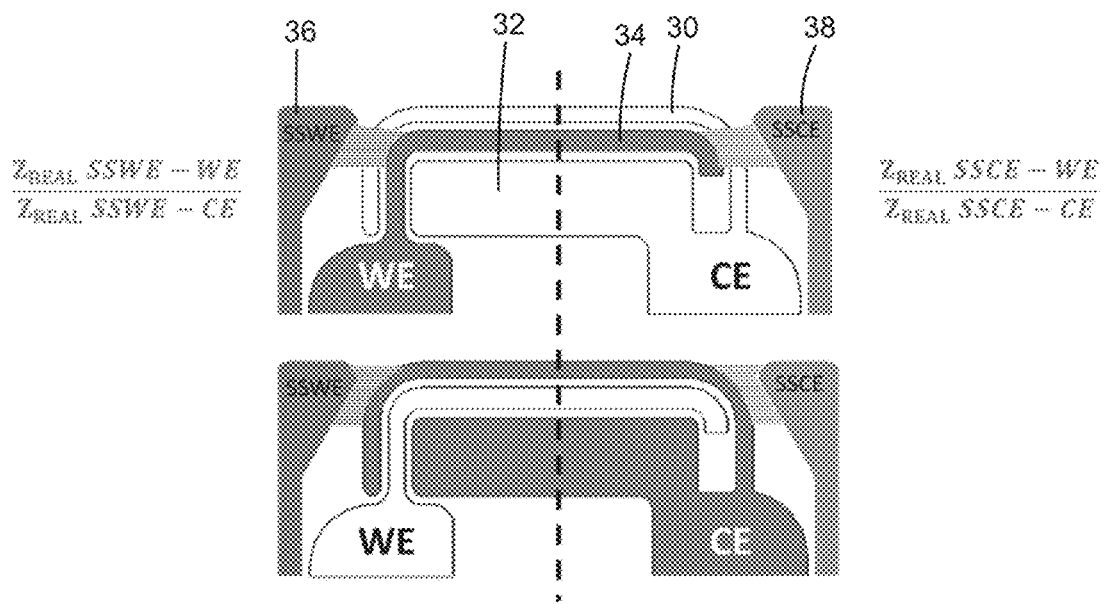
FIG. 13 illustrates a one-sided comparison between a perimeter electrode and a proximal electrode and the same perimeter electrode and a similar but more distal secondary electrode for the biosensor of FIG. 2.

The testing indicated that a two-sided comparison of ratios of $|Z|_{SSWE-CE}$ to $|Z|_{SSCE-CE}$ ratios did not provide sufficient warning of irregularities in equivalent coverage, contact resistance and electrode integrity for the SSCE 38 and SSWE 36. Thus, the electrode break check was restricted to a one-sided comparison as illustrated in FIG. 13. This modified failsafe compares the impedance between a perimeter electrode (SSCE 38 or SSWE 36) and a proximal electrode such as the primary electrode (outer counter electrode 30) (FIG. 13) and the same perimeter electrode and a similar but more distal secondary electrode (working electrode 34) (FIG. 13). A "left side" check interrogates the SSWE 36 impedances and a "right side" check interrogates the SSCE 38 impedances. By design, the impedance between the SSWE 36 and the more distant working electrode 34 should be greater than the impedance between the SSWE 36 and the closer (outer) counter electrode 30. The impedance between the SSWE 36 and either undamaged secondary electrode (outer counter electrode 30 or working electrode 34) is profoundly influenced by sample conductivity, temperature, electrode area, and metal sheet resistance.

However, these effects should be deterministic for a given sample sufficiency electrode (SSCE 38 or SSWE 36), regardless of the selected secondary electrode. The $Z_{REAL}$ (SSWE-WE)/$Z_{REAL}$ (SSWE-CE) distal/proximal impedance ratio should be unaffected by these factors and remain slightly more than unity over a wide range of sample and test conditions. Thus, if the $Z_{REAL}$ (SSWE-WE)/$Z_{REAL}$ (SSWE-CE) distal/proximal impedance ratio is less than about 1.005, it is likely because the outer counter electrode 30 is broken or defective and does not extend contiguously undisturbed as intended.

Figures 14A, 14B:
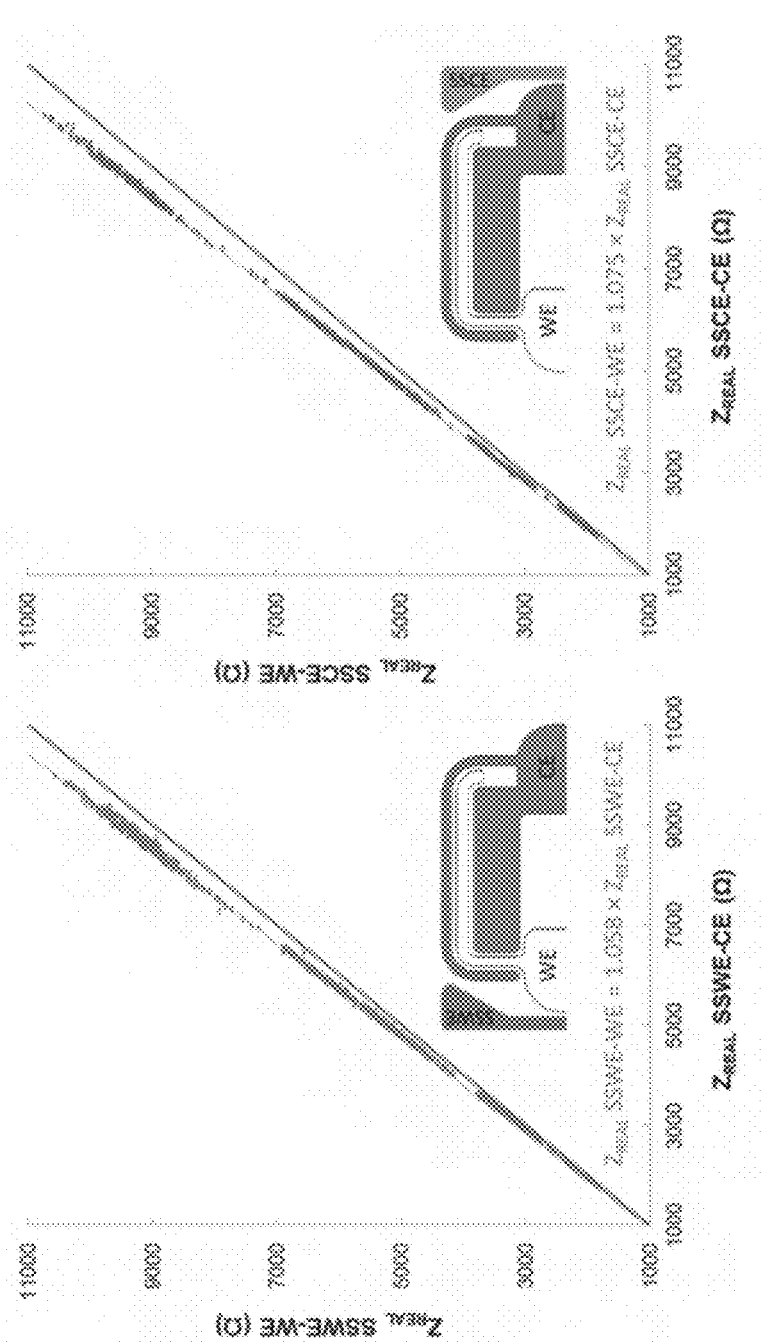
FIG. 14A plots one-sided $Z_{REAL}$ relationships for the biosensor of FIG. 13.
FIG. 14B plots one-sided $Z_{REAL}$ relationships for the biosensor of FIG. 13.

The right side check similarly interrogates the SSCE 38. If the ratio $Z_{REAL}$ (SSCE-WE)/$Z_{REAL}$ (SSCE-CE) is, between about 1.043 and about 1.100, it is most likely because the outer counter electrode 30 is broken or defective. If the $Z_{REAL}$ (SSCE-WE)/$Z_{REAL}$ (SSCE-CE) distal/proximal impedance ratio is greater than about 1.100, it is most likely due to a large $Z_{REAL}$ (SSCE-WE) impedance, indicating the working electrode 34 is broken or defective. FIGS. 14A and 14B show the one-sided $Z_{REAL}$ relationships for nominal biosensors 10 are extremely predictable over biosensor age, reagent thickness, manufacturing limits, metallization thickness, test environment as well as solution type and conductivity (HCT).

Figure 15:
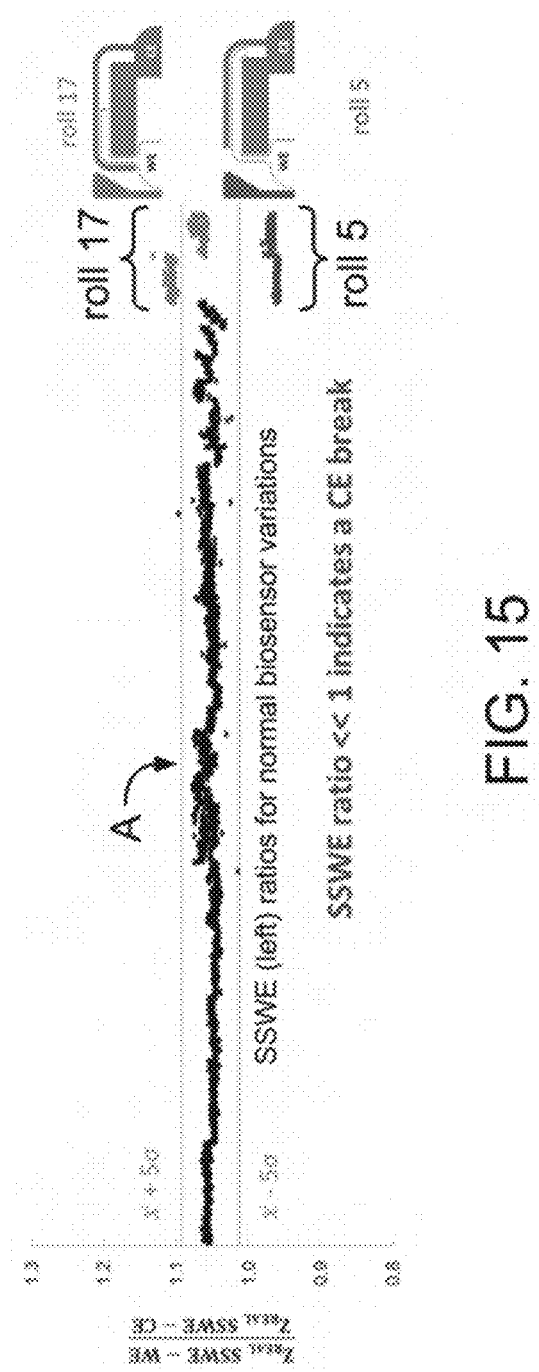
FIG. 15 plots one-sided $Z_{REAL}$ relationships from FIG. 14A and impedance ratios for aqueous test solutions and blood samples using about 2200 biosensors with nominal electrodes and similar measurements taken using about 200 biosensors with intentionally defective electrodes.
Figure 16:
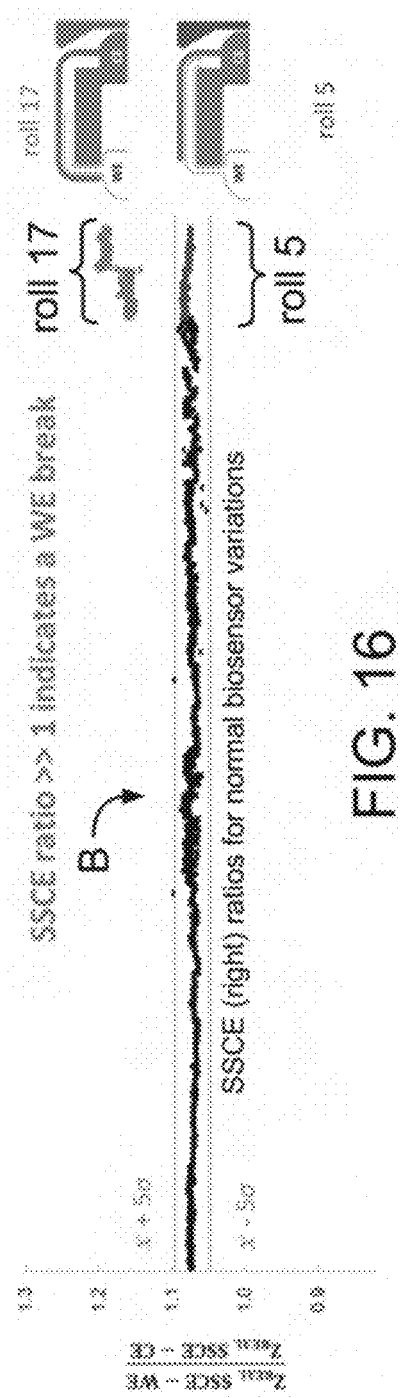
FIG. 16 plots one-sided $Z_{REAL}$ relationships from FIG. 14B and impedance ratios for about 200 linearity and blood samples for each of two intentional defects from a first test pilot.

To determine the defect detection ability, the FIGS. 14A and 14B impedance data for about 2,200 nominal biosensors 10 is plotted as impedance ratios, labeled A in FIG. 15 and labeled B in FIG. 16. Included in the FIGS. 15 and 16 are nominal mean x±5σlimits for each one-sided ratio. It was discovered that the SSCE side ratio (FIG. 16) is less variable than the SSWE side ratio (FIG. 15) although it is not evident in FIGS. 17A and 17B. Adjacent to the normal biosensor 10 variations plotted in FIGS. 15 and 16 are plotted the one-sided SSWE and SSCE impedance ratios for 200 linearity and blood samples for two intentional defects from the test pilot: roll 17 that is missing 50% of the working electrode 34 and roll 5 that is missing 25% of the outer counter electrode 30. From FIG. 15, it was discovered that the one-sided SSWE impedance ratio cannot reliably distinguish the midpoint break in the test pilot roll 17's working electrode 34 from nominal material, but easily detects the test pilot roll 5's 25% broken counter electrode. In other words, the one-sided SSWE impedance ratio is less than 1 in all of the test results which indicates there is an electrode break or defect in the outer counter electrode 30. From FIG. 16, it was discovered that the one-sided SSCE impedance ratio is ineffective at distinguishing a break in roll 5's outer counter electrode 30 from the nominal material, but reliably detects every instance of the midpoint break in the test pilot roll 17's working electrode 34. In other words, the one-sided SSCE impedance ratio is greater than 1 in all of the test results which indicates there is an electrode break or defect in the working electrode 34.

Figure 17:
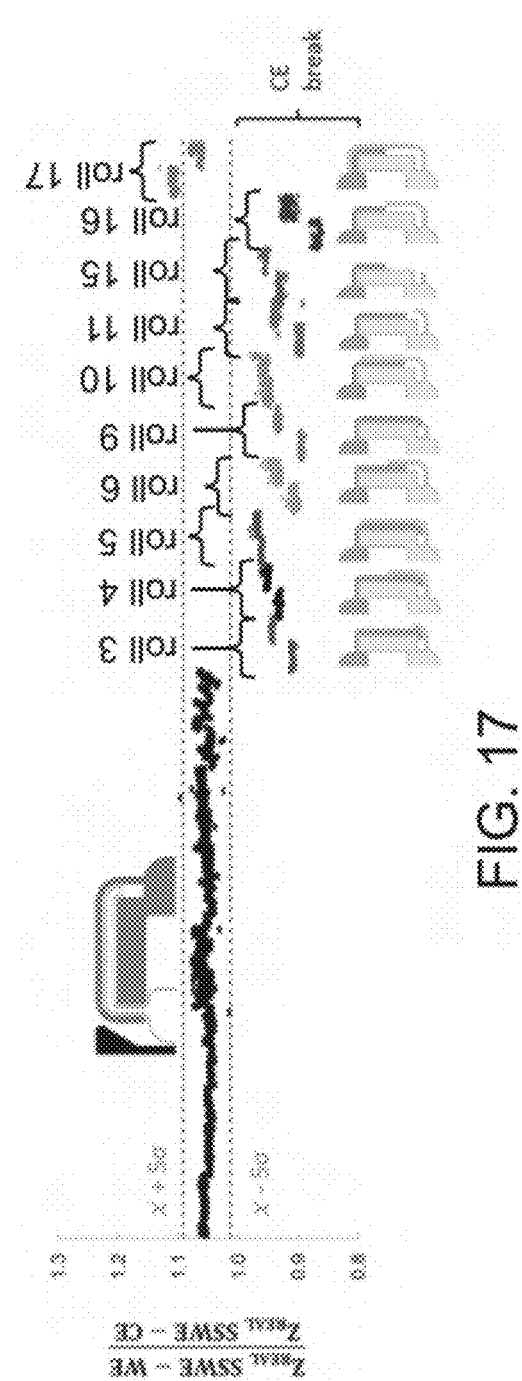
FIG. 17 plots one-sided $Z_{REAL}$ ratios for undamaged biosensors shown in FIG. 2 and the induced electrode breaks in the outer counter electrode and/or the working electrode of the biosensors shown in FIG. 2.
Figure 18:
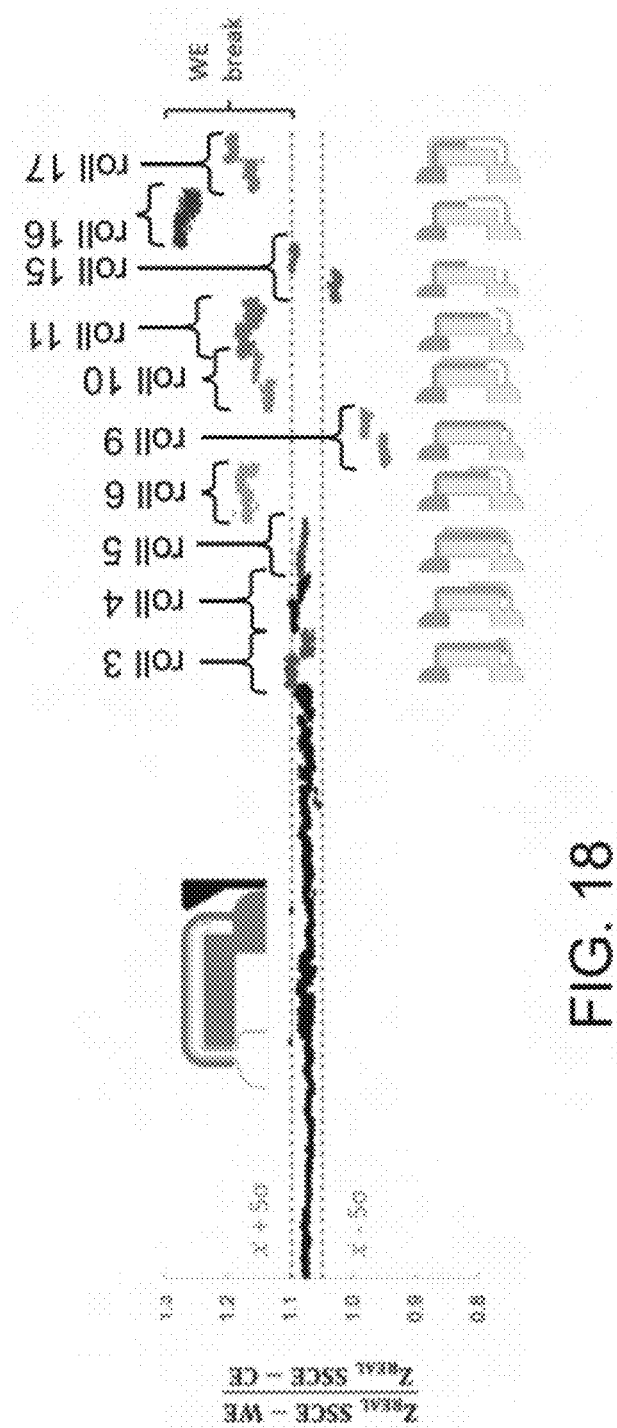
FIG. 18 plots one-sided $Z_{REAL}$ ratios for undamaged biosensors shown in FIG. 2 and the induced electrode breaks in the outer counter electrode and/or the working electrode of the biosensors shown in FIG. 2.

FIGS. 17 and 13 show the one-sided $Z_{REAL}$ ratios for linearity and blood samples on undamaged biosensors 10 with all the test pilot induced electrode breaks in rolls 3, 4, 5, 6, 9, 10, 11, 15, 16, and 17, discussed previously. FIG. 17 plots the ratio $Z_{REAL}$ (SSWE-WE)/$Z_{REAL}$ (SSWE-CE) which is intended to detect breaks in the outer counter electrode 30. This one-sided ratio reliably detects each outer counter electrode 30 defect, but cannot distinguish roll 17 that has an intact outer counter electrode 30 and a midpoint break in working electrode 34 in biosensor 10 from normal biosensors 10 that do not have any electrode breaks. FIG. 13 is the ratio $Z_{REAL}$ (SSCE-WE)/$Z_{REAL}$ (SSCE-CE) that detects a break or defect in the working electrode 34. This ratio $Z_{REAL}$ (SSCE-WE)/$Z_{REAL}$ (SSCE-CE) reliably detects the midpoint break in working electrode 34 of roll 17 "missed" by the ratio $Z_{REAL}$ (SSWE-WE)/$Z_{REAL}$ (SSWE-CE) in FIG. 17. The ratio $Z_{REAL}$ (SSCE-WE)/$Z_{REAL}$ (SSCE-CE) catches most of the remaining breaks in the working electrode 34 of the rolls 3, 4, 5, 6, 9, 10, 11, 15, 16, and 17 evaluated, but cannot distinguish intact working electrodes 34 from rolls 3, 4, and 5 from normal biosensors 10. The ratio $Z_{REAL}$ (SSCE-WE)/$Z_{REAL}$ (SSCE-CE) is also ineffective at distinguishing roll 15 (midpoint break in working electrode 34 and 5% of outer counter electrode 30 present on the biosensor 10) from normal biosensors 10 that do not have any electrode breaks, due to the small stub of the outer counter electrode 30 creating a high $Z_{REAL}$ (SSCE-CE), offsetting the elevated $Z_{REAL}$ (SSCE-WE) due to the midpoint break in working electrode 34. The ratio $Z_{REAL}$ (SSWE-WE)/$Z_{REAL}$ (SSWE-CE) readily identifies roll 15 as defective. The ratio $Z_{REAL}$ (SSCE-WE)/$Z_{REAL}$ (SSCE-CE) detection rule fails for intact working electrode 34 for roll 9. The ratio $Z_{REAL}$ (SSCE-WE)/$Z_{REAL}$ (SSCE-CE) for roll 9 is less than one because the numerator $Z_{REAL}$ (SSCE-WE) is relatively normal, but the denominator $Z_{REAL}$ (SSCE-CE) is much greater than expected due to the largely unconnected outer counter electrode 30. The ratio $Z_{REAL}$ (SSWE-WE)/$Z_{REAL}$ (SSWE-CE) and the ratio $Z_{REAL}$ (SSCE-WE)/$Z_{REAL}$ (SSCE-CE) are insensitive to variations in glucose concentration, sample type, hematocrit, temperature, reagent flow rate, capillary height, spacer placement, metallization limits, biosensors stored in a closed vial for over two years, use case exposure, raw materials, manufacturing processes, environmental conditions and test solution.

Exemplary embodiments of electrode arrangements for a biosensor are described above in detail. The apparatus and methods are not limited to the specific embodiments described herein, but rather, operations of the methods and components of the systems may be utilized independently and separately from other operations or components described herein. For example, the methods and apparatus described herein may have other industrial or consumer applications and are not limited to practice with biosensor components as described herein. Rather, one or more embodiments may be implemented and utilized in connection with other industries.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A method for detecting an electrode defect for a biosensor having a perimeter electrode, a proximal electrode, and a distal electrode, the perimeter electrode being positioned closer to the proximal electrode than to the distal electrode, comprising:
applying a liquid measuring medium to contact each of the perimeter electrode, the proximal electrode, and the distal electrode on the biosensor;
applying a first alternating voltage to the perimeter electrode and the proximal electrode;
measuring a first conductivity between the perimeter electrode and the proximal electrode;
using the first conductivity to determine a first impedance between the perimeter electrode and the proximal electrode;
applying the first alternating voltage to the perimeter electrode and the distal electrode;
measuring a second conductivity between the perimeter electrode and the distal electrode;
using the second conductivity to determine a second impedance between the perimeter electrode and the distal electrode;
determining a value comparing the first impedance and the second impedance;
determining whether the value is out of tolerance; and
providing an error message indicating an electrode defect when the value is out of tolerance.

2. The method according to claim 1, wherein the perimeter electrode is a sample sufficiency counter electrode.

3. The method according to claim 1, wherein the perimeter electrode is a sample sufficiency working electrode.

4. The method according to claim 1, wherein the proximal electrode is one of a working electrode or a counter electrode, and the distal electrode is the other of the working electrode or the counter electrode.

5. The method according to claim 1, further comprising: detecting a defect in the proximal electrode.

6. The method according to claim 1, further comprising: detecting a defect in the distal electrode.

7. The method according to claim 1, wherein the value is a ratio formed between the first impedance and the second impedance.

8. The method according to claim 7, wherein the error message is provided when the ratio is less than 1.0, the perimeter electrode is a sample sufficiency working electrode, the proximal electrode is a working electrode, and the distal electrode is a counter electrode.

9. The method according to claim 7, wherein the error message is provided when the value is greater than 1.0, the perimeter electrode is a sample sufficiency counter electrode, the proximal electrode is a working electrode, and the distal electrode is a counter electrode.

10. The method of claim 1, wherein the value is a ratio $Z_{REAL}$ (perimeter electrode-proximal electrode)/$Z_{REAL}$ (perimeter electrode-distal electrode) wherein the value being less than 1.0 indicates the distal electrode is defective.

11. The method of claim 1, wherein the value is a ratio $Z_{REAL}$ (perimeter electrode-proximal electrode)/$Z_{REAL}$ (perimeter electrode-distal electrode) wherein the value being greater than 1.0 indicates the proximal electrode is defective.

12. The method of claim 1 in which the biosensor comprises a second perimeter electrode and the applying a medium is to also contact the second perimeter electrode, the method further comprising:
applying a second alternating voltage to the second perimeter electrode and the proximal electrode;
measuring a third conductivity which is used to determine a third impedance between the second perimeter electrode and the proximal electrode;
applying the second alternating voltage to the second perimeter electrode and the distal electrode;
measuring a fourth conductivity which is used to determine a fourth impedance between the second perimeter electrode and the distal electrode;
determining a second value comparing the third impedance and the fourth impedance;
determining whether the second value is out of tolerance; and
providing a second error message when the second value is out of tolerance.

13. The method of claim 1 in which the electrode defect is an electrode breakage.

14. The method of claim 13 in which the error message indicates an electrode breakage.

15. A measuring instrument for error checking a biosensor, the instrument comprising:
contacts which electrically connect to a first perimeter electrode, a second perimeter electrode, a proximal electrode, and a distal electrode on the biosensor;

electronics which generate a test voltage and detect sensor signals from the first perimeter electrode, the second perimeter electrode, the proximal electrode, and the distal electrode;

a processor programmed to:

apply an alternating voltage to two of the electrodes of the biosensor wherein one of the electrodes is either the first perimeter electrode or the second perimeter electrode, and the second of the electrodes is either the proximal electrode or the distal electrode and to measure conductivity which is used to determine a first impedance between the two of the electrodes;

apply the alternating voltage to the remaining two electrodes of the biosensor and measure conductivity which is used to determine a second impedance between the remaining two electrodes;

determine a value using the first impedance and the second impedance; and provide an error message when the value is out of tolerance; and an output unit which provides the error message.

16. The instrument of claim 15, wherein the value is a ratio formed between the first impedance and the second impedance.

17. The instrument according to claim 15, wherein the providing the error message occurs when the value is less than 1.0, the first perimeter electrode is a sample sufficiency working electrode, the proximal electrode is a working electrode, and the distal electrode is a counter electrode.

18. The instrument according to claim 15, wherein the providing the error message occurs when the value is greater than 1.0, the second perimeter electrode is a sample sufficiency counter electrode, the proximal electrode is a working electrode, and the distal electrode is a counter electrode.

19. A method for detecting an electrode breakage for a biosensor having first, second and third electrodes, the first electrode being positioned closer to the second electrode than to the third electrode, comprising:

applying a liquid measuring medium to contact each of the first, second and third electrodes;

applying an alternating voltage to the first electrode and the second electrode;

determining a first impedance between the first electrode and the second electrode;

applying the alternating voltage to the first electrode and the third electrode;

determining a second impedance between the first electrode and the third electrode;

identifying an electrode breakage based on a comparison of the first impedance and the second impedance.

20. The method of claim 19 and which further includes providing an error message indicating the electrode breakage.

21. The method of claim 19 and which further comprises:

determining a value comparing the first impedance and the second impedance;

determining whether the value is out of tolerance; and providing an error message indicating an electrode breakage when the value is out of tolerance.

22. The method of claim 21 in which the value is a ratio between the first impedance and the second impedance, and in which the value is out of tolerance when the value is less than 1.0.

* * * * *